United States Patent [19]

Drewlow

[11] Patent Number: Plant 7,285

[45] Date of Patent: Jul. 31, 1990

[54] BEGONIA PLANT NAMED CAMELOT

[75] Inventor: Lyndon W. Drewlow, Ashtabula, Ohio

[73] Assignee: Mikkelsens, Inc., Ashtabula, Ohio

[21] Appl. No.: 360,423

[22] Filed: Jun. 2, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Begonia plant named Camelot having large, bright yellow flowers, a floriferous habit, relatively large leaves, strong stamens and petioles, compact growth habit, early flowering and long lasting flowers, and the ability to be propagated readily from both leaf and stem cuttings.

1 Drawing Sheet

The present invention relates to a new and distinctive cultivar of Begonia plant, botanically known as *Begonia hiemalis*×*Begonia fotsch,* and known by the cultivar name Camelot.

The new cultivar was discovered as a mutation of St. Helena, disclosed in U.S. Plant Pat. No. 6,329, and was observed in a group of 15 cm flowering plants of the parent, and identified as 87-7002.

Asexual reproduction by stem and/or leaf cuttings has reproduced the unique features of the new culivar through successive propagations.

The following characteristics distinguish the new begonia from both its parents and other begonias commercially known and used in the floriculture industry. In the comparisons, references to previously patented cultivars have been made, including Ballet (U.S. Plant Pat. No. 4,743), Romance Too (U.S. Plant Pat. No. 5,953), and the parent cultivar St. Helena (U.S. Plant Pat. No. 6,329).

1. Camelot is a bright yellow flowered cultivar similar to Ballet, with Romance Too being a lighter shade of yellow and St. Helena orange in color.

2. Flower size is larger than Ballet and Romance Too, and similar in size to St. Helena. Camelot, St. Helena and Romance Too have rounded flowers while Ballet is more obovate.

3. Camelot is more double flowered than Ballet and Romance Too, while St. Helena is similar.

4. Plant size and shape are similar to St. Helena, with Ballet and Romance Too being more compact.

5. Camelot tends to average 5 blooms per raceme while Romance Too averages 4 blooms per raceme, and St. Helena and Ballet only 3 blooms per raceme.

6. Camelot has the least amount of reddish tinge to leaf margins of young leaves and to the underside of the young leaf when compared to St. Helena, Romance Too and Ballet.

7. Camelot and Romance Too have green main stems on mature plants while Ballet has a reddish cast to the basal area of the main stem, and St. Helena has a reddish cast to the entire main stem.

8. Camelot and St. Helena have slightly larger leaves than Ballet and Romance Too. All four cultivars are similar in leaf color (dark green) and in texture.

9. Camelot has strong stems and petioles; compact growth habit with good top flowering makes Camelot suitable for 10, 15 or 25 cm pot.

10. Camelot propagates readily from both stem and leaf cuttings.

11. Early flowering; a flowering plant is finished in a 15 cm pot in 18 weeks from a pinched stem cutting.

12. Flowers are long lasting and will continue to bloom under long day conditions.

13. Flowers do not shatter when shipped.

14. No female flowers and no pollen in the full double flowers.

15. Good balance between leaf size and plant size.

The accompanying colored photograph illustrates in top perspective view the overall appearance of the new cultivar, showing the colors as true as it is reasonably possible to obtain in a colored reproduction of this type. The photo was taken in December 1988.

The following is a detailed description of my new Begonia cultivar based on plants produced under commercial practices in Ashtabula, Ohio, under greenhouse conditions. Color references are made to The Royal Horticultural Society Colour Chart except where general color terms of ordinary dictionary significance are used.

Parentage: Mutation of St. Helena and identified as 87-7002.

Propagation:

(A) *Type cutting.*—Leaf cuttings root in 18 days in summer and 24 days in winter at 21° C.; rooting stem cuttings 2 to 3 cm long at the same temperature takes 16 days in summer and 18 days in winter.

(B) *Rooting habit.*—Abundant, fine, fibrous.

(C) *Time for shoot development.*—For leaf cuttings, 10 weeks in summer to 13 weeks in winter to obtained shoots 4 to 5 cm long; for stem cuttings, shoot 5–6 cm long are obtained in 5 weeks in summer and 6 weeks in winter.

Plant Description:

(A) *Form.*—Upright, good stem strength for self-support, compact, short internodes. Suitable for 10 and 15 cm pot plant production.

(B) *Habit of growth.*—Vigorous, fast upright growth with good branching from base of plant when pinched. Usually vegetative shoots are formed at the basal nodes and flower shoots at the higher nodes.

(C) *Foliage.*—Leaves simple, alternate, borne on strong petioles 5–6 mm in diameter on mature leaves. (1) Size: Can vary greatly with leaf position on plant and number of shoots per plant; environment can also affect leaf size; 10 to 12 cm across on mature leaves. (2) Shape: Ovate to almost orbicular, lobes just touch on mature leaves near petiole attachment. (3) Texture: Leathery, glabrous. (4) Margin: Serrated. (5) Color: Young foliage: Top side 146A–146B with a reddish cast; under side 146D in veinal area with heavy red cast. Mature foliage: 137A; 146C in veinal area with reddish cast to rest of area. (6) Venation: Palmate; 5 to 7 major veins.

(A) *Flowering habits.*—Flowering in racemes, with 5 blooms per raceme the most common; several racemes in bloom at one time; flowering continues more or less indefinitely.

(B) *Natural flowering season.*—Will flower year around without controlling day length; plants will flower earlier and more abundantly if subjected to a reduced day length of 12 hours.

(C) *Flower buds.*—20 mm long and 30 mm wide just before opening; tepals are entire to slightly serrated around margins; color 8C just before opening and 9D when immature.

(D) *Flowers borne.*—On strong upright peduncles bright green in color and 5 mm in diameter.

(E) *Quality.*—Average of 5 per peduncle, opening in sequence as the raceme develops; varies with number of flowering shoots per plants.

(F) *Tepals.*—(1) Shape: Flat and nearly rounded. (2) Color: Top side in winter when opening, between 13A and 13B, fading to between 13B and 13C; under side 8C. (3) Number of tepals: 20 to 30 or more. (4) Size of tepals: 35 to 40 mm in diameter when fully open. (5) Flower size: 5 to 6 cm in diameter.

(G) *Reproductive organs.*—(1) Stamens: None as plant is fully double with anthers appearing as petals. (2) Pistels: None.

Disease resistance: Camelot has shown good disease resistance to powdery mildew.

I claim:

1. A new and distinct Begonia plant named Camelot, as illustrated and described.

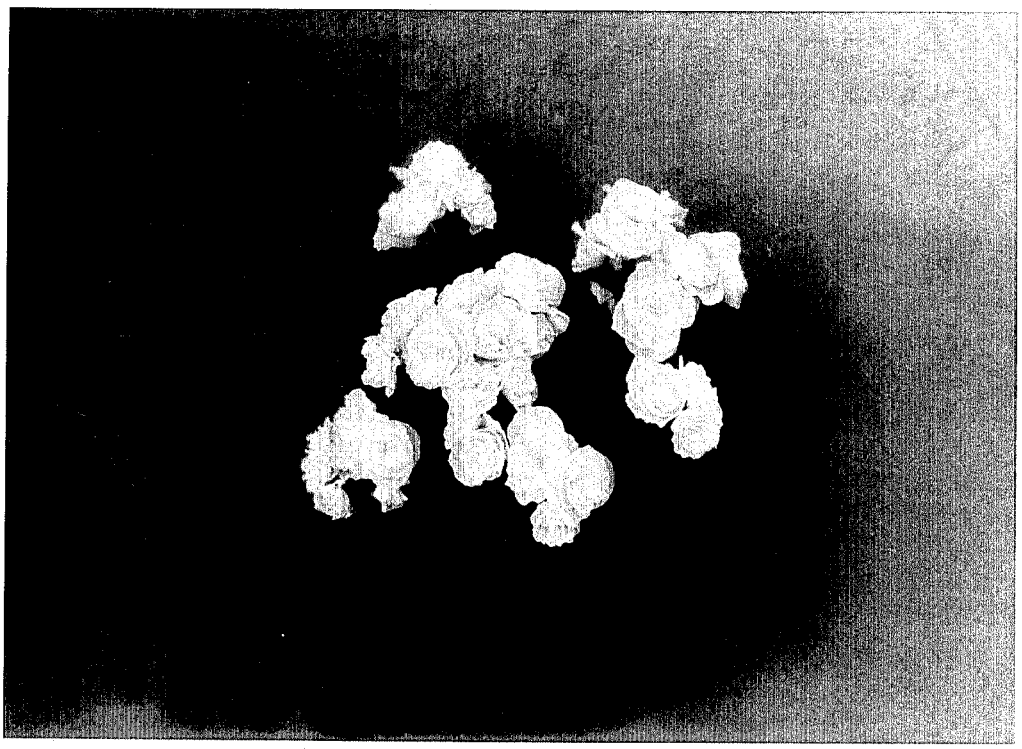

* * * * *